United States Patent
Rieder et al.

(10) Patent No.: US 7,080,564 B2
(45) Date of Patent: *Jul. 25, 2006

(54) VIBRATORY TRANSDUCER

(75) Inventors: Alfred Rieder, Landshut (DE); Wolfgang Drahm, Erding (DE)

(73) Assignee: Endress + Hauser Flowtec AG, Reinach (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/212,718

(22) Filed: Aug. 29, 2005

(65) Prior Publication Data

US 2006/0000292 A1 Jan. 5, 2006

Related U.S. Application Data

(63) Continuation of application No. 10/431,573, filed on May 8, 2003.

(60) Provisional application No. 60/393,116, filed on Jul. 3, 2002, provisional application No. 60/400,047, filed on Aug. 2, 2002.

(30) Foreign Application Priority Data

| May 8, 2002 | (DE) | ................................ 102 20 827 |
| Aug. 1, 2002 | (DE) | ................................ 102 35 322 |

(51) Int. Cl.
*G21F 1/84* (2006.01)

(52) U.S. Cl. .................................................. 73/861.357

(58) Field of Classification Search ........... 73/861.351, 73/861.352, 861.355, 861.354, 861.357
See application file for complete search history.

(56) References Cited

U.S. PATENT DOCUMENTS

| 5,323,658 | A | * | 6/1994 | Yao et al. | ............... 73/861.357 |
| 5,663,509 | A | * | 9/1997 | Lew et al. | ............. 73/861.357 |
| 5,700,958 | A | * | 12/1997 | Lew et al. | ............. 73/861.357 |
| 6,397,685 | B1 | * | 6/2002 | Cook et al. | ............ 73/861.357 |
| 6,666,098 | B1 | * | 12/2003 | Drahm et al. | .......... 73/861.355 |
| 6,684,716 | B1 | * | 2/2004 | Ohnishi et al. | ........ 73/861.357 |
| 6,691,583 | B1 | * | 2/2004 | Rieder et al. | .......... 73/861.357 |
| 6,711,958 | B1 | * | 3/2004 | Bitto et al. | ............. 73/861.355 |
| 6,718,615 | B1 | * | 4/2004 | Van Cleve et al. | ........ 29/592.1 |
| 6,840,109 | B1 | * | 1/2005 | Drahm et al. | ................. 73/650 |
| 6,851,323 | B1 | * | 2/2005 | Rieder et al. | .......... 73/861.357 |

* cited by examiner

*Primary Examiner*—Michael Cygan
(74) *Attorney, Agent, or Firm*—Bacon & Thomas

(57) ABSTRACT

To conduct a fluid, the transducer has a flow tube which in operation is vibrated by an excitation assembly and whose inlet-side and outlet-side vibrations are sensed by means of a sensor arrangement. To produce shear forces in the fluid, the flow tube is at least intermittently excited into torsional vibrations about a longitudinal flow-tube axis. The transducer further comprises a torsional vibration absorber which is fixed to the flow tube and which in operation covibrates with the torsionally vibrating flow tube, thus producing reactive torques which at least partially balance torques developed in the vibrating flow tube. One of the advantages of the transducer disclosed is that it is dynamically balanced to a large extent even in the face of variations in fluid density or viscosity.

35 Claims, 5 Drawing Sheets

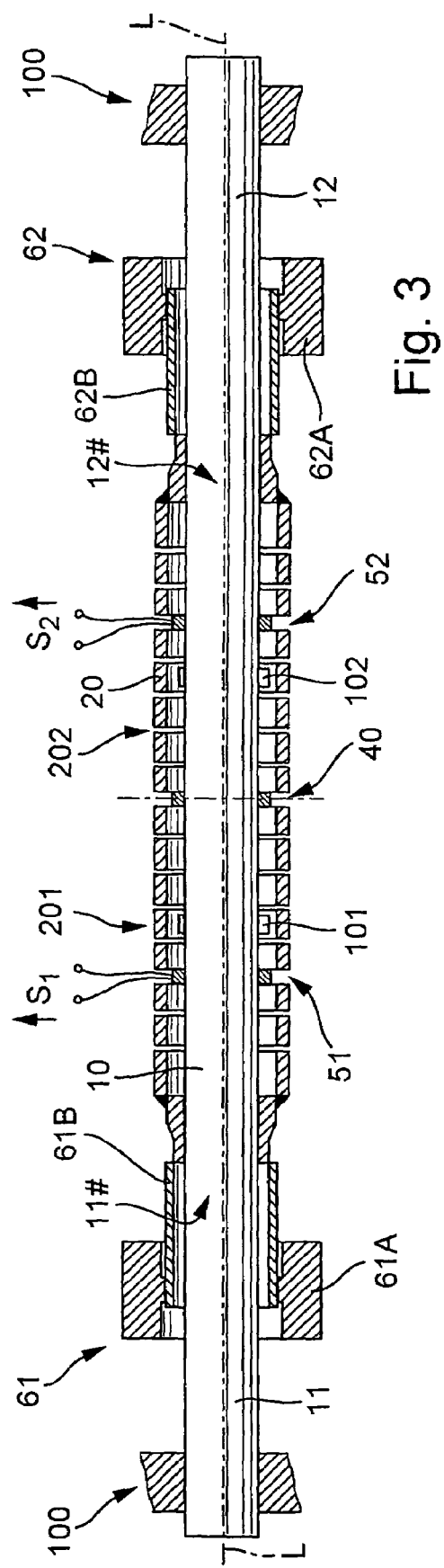
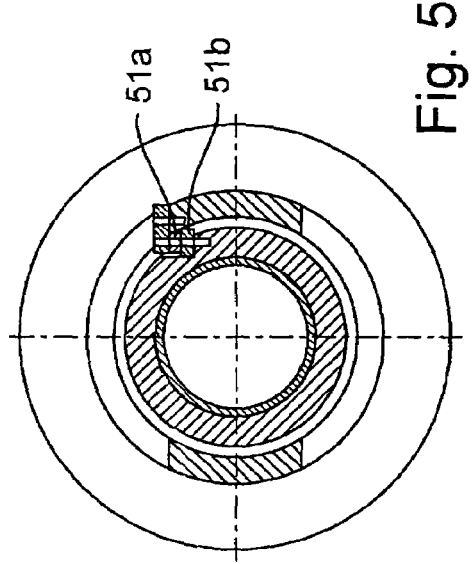
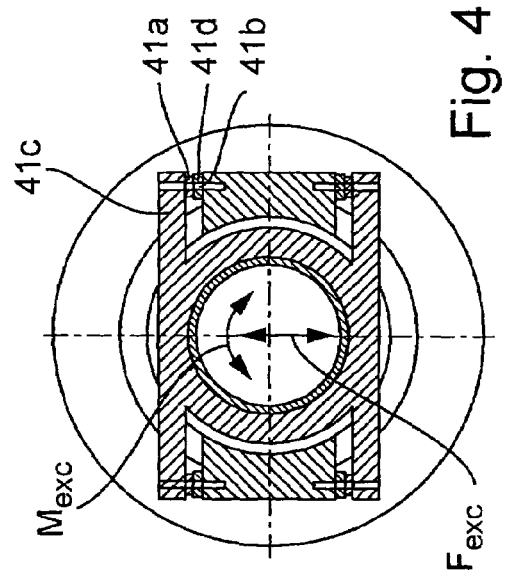

VIBRATORY TRANSDUCER

This application claims the benefit under 35 USC 119 of the following prior filed provisional applications: 60/393,116, filed Jul. 3, 2002; and 60/400,047, filed Aug. 2, 2002; and is a continuation of nonprovisional application: Ser. No. 10/431,573 filed May 8, 2003 which has been allowed but has not yet issued.

FIELD OF THE INVENTION

This invention relates to a vibratory transducer which is particularly suited for use in a viscometer, a viscometer-densimeter, or a viscometer-mass flowmeter.

BACKGROUND OF THE INVENTION

To determine the viscosity of a liquid flowing in a pipe, use is frequently made of meters which, using a vibratory transducer, comprising a flow tube communicating with the pipe and control and evaluation electronics connected thereto, induce shear or friction forces in the fluid and derive therefrom a measurement signal representing the viscosity.

U.S. Pat. No. 4,524,610, U.S. Pat. No. 5,253,533, U.S. Pat. No. 6,006,609, or EP-A 1 158 289, for example, disclose in-line viscometers, i.e., viscometers connectable into a fluid-conducting pipe, with a vibratory transducer which responds to the viscosity of the fluid flowing in the pipe and comprises:
- a single straight flow tube for conducting the fluid which vibrates in operation and communicates with the pipe via an inlet tube section and an outlet tube section;
- an excitation assembly which in operation excites at least part of the flow tube into torsional vibrations about an axis of vibration aligned with the flow tube; and
- a sensor arrangement for locally sensing vibrations of the flow tube.

As is well known, straight flow tubes, when excited into torsional vibrations about an axis aligned with the flow tube, cause shear forces to be produced in the fluid flowing through the tube, whereby vibrational energy is removed from the torsional vibrations and dissipated to the fluid. This results in the torsional vibrations of the flow tube being damped, so that additional excitation energy must be supplied to the flow tube to maintain those vibrations. The applied excitation energy can be measured in a suitable manner, and the viscosity of the fluid can be derived therefrom.

In operation, the flow tubes of such transducers, which are used in in-line viscometers, for example, are generally excited at an instantaneous resonance frequency of a fundamental torsional mode, particularly with the vibration amplitude maintained at a constant value.

It is also common practice to excite the flow tubes for viscosity measurements, simultaneously or alternately with the torsional mode, into flexural vibrations, preferably at a resonance frequency of a fundamental flexural mode, see also the above referred to U.S. Pat. No. 4,524,610. Since this flexural resonance frequency is also dependent on the instantaneous density of the fluid in particular, such meters can also be used to measure the density of fluids flowing in pipes.

Compared with the use of bent flow tubes for viscosity measurements, the use of straight flow tubes vibrating in the manner described above, as is well known, has the advantage that shear forces are induced in the fluid over virtually the entire length of the flow tube, particularly with a great depth of penetration in the radial direction, so that very high sensitivity of the transducer to the viscosity to be measured can be achieved. Another advantage of straight flow tubes is that they can be drained residue-free with a high degree of reliability in virtually any position of installation, particularly after a cleaning operation performed in-line. Furthermore, such flow tubes are much easier and, consequently, less expensive to manufacture than, for example, an omega-shaped or helically bent flow tube.

An essential disadvantage of the prior art transducers lies in the fact that in operation, torsional vibrations can be transmitted from the transducer via the flow tube and any transducer case that may be present to the connected pipe. This, in turn, may result in a zero shift and, thus, in measurement inaccuracies. Furthermore, the loss of vibrational energy to the transducer's environment may result in a substantial deterioration of efficiency and possibly also in a degradation of the signal-to-noise ratio in the measurement signal.

SUMMARY OF THE INVENTION

It is therefore an object of the invention to provide a vibratory transducer which is particularly suited for a viscometer and which in operation, even if it uses only a single, particularly straight, flow tube, is dynamically well balanced over a wide fluid density range and nevertheless has comparatively little mass.

To attain the object, the invention provides a vibratory transducer for a fluid flowing in a pipe, the transducer comprising a flow tube for conducting the fluid which in operation vibrates at a predeterminable frequency, an excitation assembly acting on the flow tube for vibrating the flow tube, a sensor arrangement for sensing vibrations of the flow tube, and a torsional vibration absorber fixed to the flow tube. The flow tube communicates with the pipe via an inlet tube section, ending in an inlet end of the flow tube, and via an outlet tube section, ending in an outlet end of the flow tube. Primarily in order to produce shear forces in the fluid, in operation, the flow tube performs, at least intermittently, torsional vibrations about a longitudinal flow-tube axis at an instantaneous torsional frequency. To reduce or avoid the dissipation of vibrational energy from the transducer to the connected pipe, in operation, the torsional vibration absorber is a least partially vibrated out of phase with the vibrating flow tube.

In a first embodiment of the invention, the vibrating torsional vibration absorber is driven only by the vibrating flow tube.

In a second embodiment of the invention, the torsional vibration absorber is fixed to the flow tube on the inlet and outlet sides.

In a third embodiment of the invention, the torsional vibration absorber has a torsional natural frequency greater than 0.8 times the vibration frequency of the flow tube.

In a fourth embodiment of the invention, the torsional vibration absorber has a torsional natural frequency less than 1.2 times the vibration frequency of the flow tube.

In a fifth embodiment of the invention, the torsional vibration absorber is formed by an inlet-side absorber subunit and an outlet-side absorber subunit.

In a sixth embodiment of the invention, the transducer comprises a transducer case coupled to the flow tube on the inlet and outlet sides.

In a seventh embodiment of the invention, the transducer comprises an antivibrator fixed to the flow tube at the inlet and outlet ends, particularly an antivibrator coaxial with the flow tube.

In an eighth embodiment of the invention, additional masses are provided on the flow tube.

A basic idea of the invention is to dynamically balance torques developed by the torsionally vibrating flow tube with equal reactive torques generated by means of the torsional vibration absorber, which, for example, may be driven only by the flow tube.

One advantage of the invention lies in the fact that the transducer, despite possible operational variations in the density and/or viscosity of the fluid, is balanced in a simple and robust manner such that internal torques can be largely kept away from the connected pipe. Another advantage is that as a result of this constructionally very simple vibration isolation, the transducer according to the invention can be made very compact and very light.

BRIEF DESCRIPTION OF THE DRAWINGS

The invention and further advantages will become more apparent by reference to the following description of an embodiment when taken in conjunction with the accompanying drawings. Like reference characters have been used to designate like parts throughout the various figures; reference characters that were already assigned have been omitted in subsequent figures if this contributes to clarity. In the drawings:

FIG. 3 is a sectional side view of the transducer of FIG. 2;

FIG. 4 is a first cross-sectional view of the transducer of FIG. 2;

FIG. 5 is a second cross-sectional view of the transducer of FIG. 2;

DETAILED DESCRIPTION OF EXEMPLARY EMBODIMENTS

Figure 1:
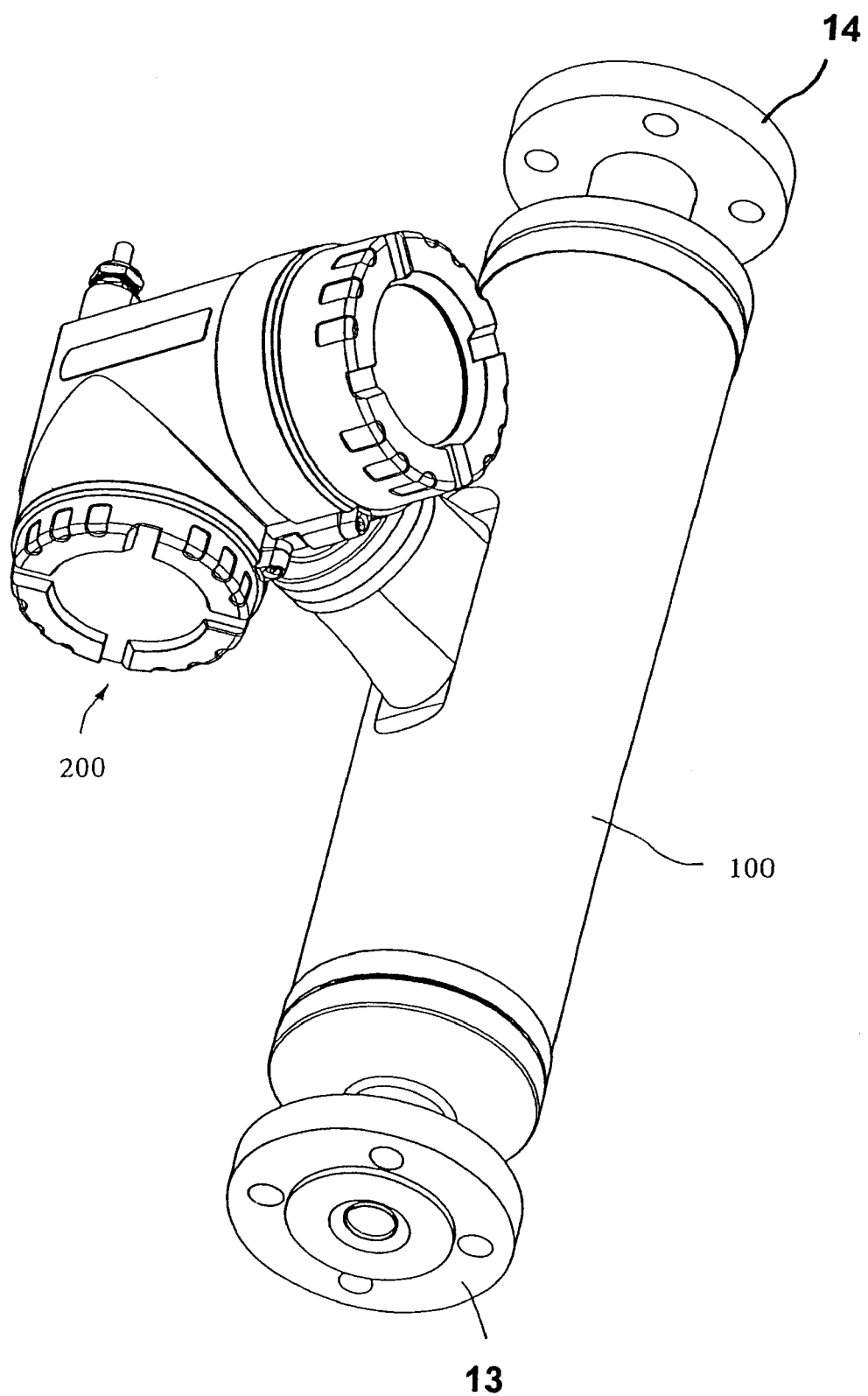
FIG. 1 shows a meter designed to be inserted in a pipe for measuring the viscosity of a fluid flowing in the pipe.

While the invention is susceptible to various modifications and alternative forms, exemplary embodiments thereof have been shown by way of example in the drawings and will herein be described in detail. It should be understood, however, that there is no intent to limit the invention to the the particular forms diclosed, but on the contrary, the intention is to cover all modifications, equivalents, and alternatives falling within the spirit and scope of the invention as defined by the intended claims.

FIG. 1 shows a meter designed to be inserted in a pipe (not shown) for measuring the viscosity of a fluid flowing in the pipe. In addition, the meter may also designed to measure the mass flow rate and/or the density of the fluid. It comprises a vibratory transducer through which the fluid to be measured flows in operation. FIGS. 2 to 6 show schematically embodiments and developments of such vibratory transducers.

To conduct the fluid, the transducer comprises an essentially straight flow tube 10, particularly a single tube, which in operation performs, at least intermittently, torsional vibrations about its longitudinal axis and is thus repeatedly elastically deformed.

To permit flow of fluid through flow tube 10, the latter is connected to a fluid-conducting pipe (not shown) via an inlet tube section 11 and an outlet tube section 12. Advantageously, flow tube 10, inlet tube section 11, and outlet tube section 12, which are aligned with each other and with an imaginary longitudinal axis L, are integrally formed, so that a single tubular semifinished product, for example, can be used for their manufacture; if necessary, however, flow tube 10 and tube sections 11, 12 may also be made from separate semifinished products that are subsequently joined together, for instance welded together. For flow tube 10, virtually any of the materials commonly used for such transducers, e.g., steel, titanium, zirconium, etc., may be used.

If the transducer is to be nonpermanently connected with the pipe, a first flange 13 and a second flange 14 may formed on inlet tube section 11 and outlet tube section 12, respectively; if necessary, however, inlet and outlet tube sections 11, 12 may also be connected with the pipe directly, for instance by welding or brazing.

Furthermore, as shown schematically in FIG. 1, an external support system 100, here shown in the form of a transducer case receiving or enclosing the flow tube 10, is fixed to inlet and outlet tube sections 11, 12, see FIGS. 1 and 3.

To produce friction forces in the fluid that correspond to the viscosity of the fluid, in operation, flow tube 10 is at least intermittently excited into torsional vibrations, particularly in the range of a torsional natural resonance frequency, such that it is twisted about its longitudinal axis L essentially according to a torsional natural vibration mode shape, cf., for instance, U.S. Pat. No. 4,524,610, U.S. Pat. No. 5,253, 533, U.S. Pat. No. 6,006,609, or EP-A 1 158 289.

The flow tube 10 is excited at a torsional frequency $f_{excT}$ corresponding as exactly as possible to a natural resonance frequency of that fundamental torsional eigenmode in which flow tube 10 is twisted essentially unidirectionally over its entire length. In the case of a flow tube 10 of special steel with a nominal diameter of 20 mm, a wall thickness of about 1.2 mm, and a length of about 350 mm and with attachments (see below), a natural resonance frequency of this fundamental torsional eigenmode may be of the order of about 1500 to 2000 Hz, for example.

Figure 7A:
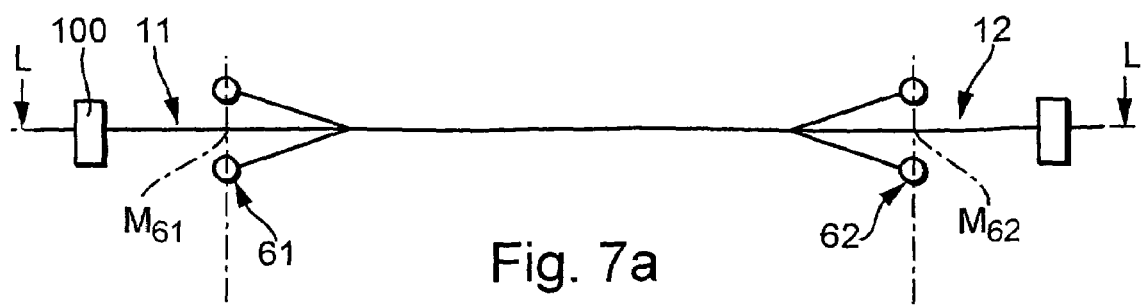
FIGS. 7a, b show schematically elastic lines of the flow tube and of an antivibrator oscillating in a flexural mode.
Figure 7B:
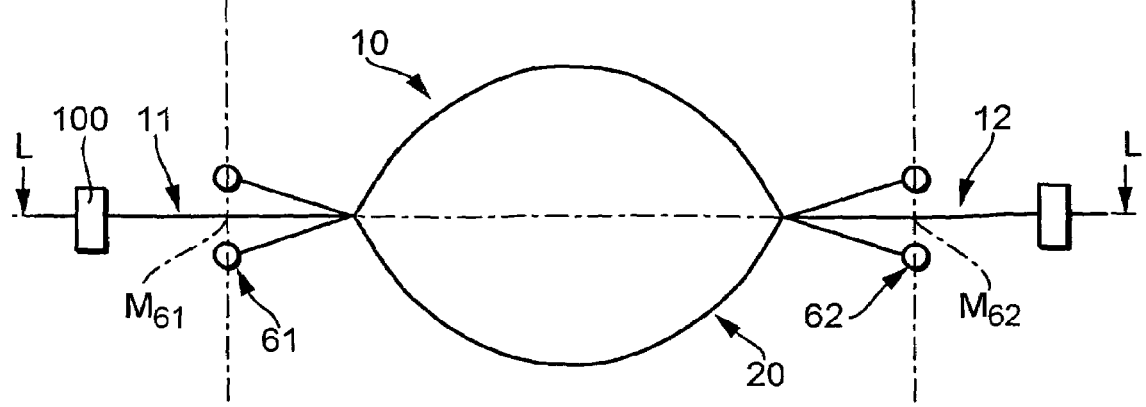

In an embodiment of the invention, during operation of the transducer, flow tube 10, in addition to being excited into torsional vibrations, is excited, particularly simultaneously therewith, into flexural vibrations in such a way as to be deflected essentially according to a natural first flexural vibration mode shape. To this end, flow tube 10 is excited at a flexural vibration frequency corresponding as exactly as possible to a lowest natural flexural resonance frequency of flow tube 10, so that the vibrating, but empty flow tube 10, as shown schematically in FIGS. 7a and 7b, is deflected essentially symmetrically with respect to a central axis perpendicular to the longitudinal axis and has a single antinode. In the case of a flow tube 10 of special steel with a nominal diameter of 20 mm, a wall thickness of about 1.2 mm, and a length of about 350 mm as well as with the usual attachments, for example, this lowest flexural resonance frequency may be of the order of about 850 to 900 Hz.

When a fluid flows through the pipe, so that the mass flow rate m is nonzero, Coriolis forces are induced in the fluid by flow tube 10 vibrating in a flexural mode. The Coriolis forces react on flow tube 10, thus causing an additional deformation (not shown) of flow tube 10 according to a natural second flexural vibration mode shape, which is coplanar with the first flexural vibration mode shape. The instantaneous shape of the deformation of flow tube 10, particularly in regard to its amplitudes, is also dependent on the instantaneous flow rate m. The second flexural vibration mode shape, the so-called Coriolis mode, may be, for instance, an asymmetric flexural vibration mode shape with two or four antinodes, as is usual with such transducers.

To generate mechanical vibrations of flow tubes 10, the transducer further comprises an excitation assembly 40, particularly an electrodynamic exciter. Excitation assembly 40 serves to convert electric excitation energy $E_{exc}$ supplied from control electronics (not shown), for instance with a regulated current and/or a regulated voltage, into an excitation moment $M_{exc}$ which acts on flow tube 10, for instance in a pulsed manner or harmonically, and elastically deforms the tube in the manner described above, and, if flow tube 10 is additionally excited into flexural vibrations, into a laterally acting excitation force. The excitation moment $M_{exc}$ may be bidirectional as shown schematically in FIG. 4 or 6, or unidirectional, and be adjusted in amplitude, for instance by means of a current-and/or voltage-regulator circuit, and in frequency, for instance by means of a phase-locked loop, in the manner familiar to those skilled in the art. From the electric excitation energy $E_{exc}$ necessary to maintain the torsional vibrations and the contingently additionally excited flexural vibrations of flow tube 10, the viscosity of the fluid can be derived in the manner familiar to those skilled in the art, cf. in particular U.S. Pat. No. 4,524,610, U.S. Pat. No. 5,253,533, U.S. Pat. No. 6,006,609, or EP-A 1 158 289.

The excitation assembly 40 may be, for example, a simple solenoid with a cylindrical excitation coil which is attached to the transducer case 100 and, in operation, is traversed by a suitable excitation current, and with a permanent magnetic armature which is fixed to the outside flow tube 10, particularly at the midpoint thereof, and rides, at least in part, in the excitation coil. Excitation assembly 40 can also be implemented with one or more electromagnets as shown in U.S. Pat. No. 4,524,610, for example.

To detect vibrations of flow tube 10, a sensor system as is commonly used for such transducers may be employed which senses the motions of flow tube 10, particularly on the inlet and outlet sides thereof, by means of at least a first sensor 51, but contingently also by means of a second sensor 52, and converts them into corresponding sensor signals $S_1$, $S_2$. Sensors 51, 52 may be, for example, electrodynamic velocity sensors as shown schematically in FIG. 1, which perform relative vibration measurements, or electrodynamic displacement sensors or acceleration sensors. Instead of electrodynamic sensor systems, sensor systems using resistive or piezoelectric strain gages or optoelectronic sensor systems may be used to detect the vibrations of flow tube 10.

As mentioned above, on the one hand, the torsional vibrations are damped by a desired energy loss to the fluid, which is sensed, particularly for the purpose of measuring viscosity. On the other hand, however, vibrational energy may also be removed from the vibrating flow tube 10 if components mechanically coupled to the flow tube, such as transducer case 100 or the connected pipe, are also excited into vibration. While the energy loss to case 100, even though undesired, could still be calibrated, at least the energy loss to the transducer's environment, particularly to the pipe, occurs in a practically nonreproducible or even unpredeterminable manner.

To suppress such a loss of torsional vibration energy to the environment, the transducer comprises a torsional vibration absorber 60, which is fixed to flow tube 10 on the inlet and outlet sides. According to the invention, torsional vibration absorber 60 serves to absorb at least part of the torsional vibration energy lost by the single flow tube 10 being twisted about its longitudinal axis L, thus keeping this energy away from the transducer's environment, particularly from the pipe connected to the transducer. To this end, at least one of the torsional resonance frequencies of the torsional vibration absorber is tuned as precisely as possible to the torsional frequency $f_{excT}$, at which the flow tube 10 is predominant-ly vibrated in operation. As a result, at least portions of the torsional vibration absorber 60 perform torsional vibrations which are out of phase with, particularly opposite in phase to, torsional vibrations of flow tube 10.

In addition, the torsional vibration absorber tuned in this way is fixed to flow tube 10 in such a manner that even with the absorber caused to vibrate, particularly in phase opposition to flow tube 10, the inlet tube section and the outlet tube section are substantially free of torsional stress.

The use of such a torsional vibration absorber is predicated particularly on recognition that the flow tube 10, vibrated in the above-described manner, has at least one torsional resonance frequency which, in contrast to its flexural resonance frequencies, for example, is correlated with the density or viscosity of the fluid only to a very small degree, and which can thus be maintained substantially constant in operation. Accordingly, at least one of the torsional resonance frequencies of such a torsional vibration absorber can be tuned comparatively precisely to the torsional resonance frequency of the flow tube to be expected in operation. At least for the above-described case where excitation assembly 40 is connected with flow tube 10 and transducer case 100, the vibrating torsional vibration absorber is driven indirectly, namely virtually exclusively by the vibrating flow tube 10.

Figure 6:
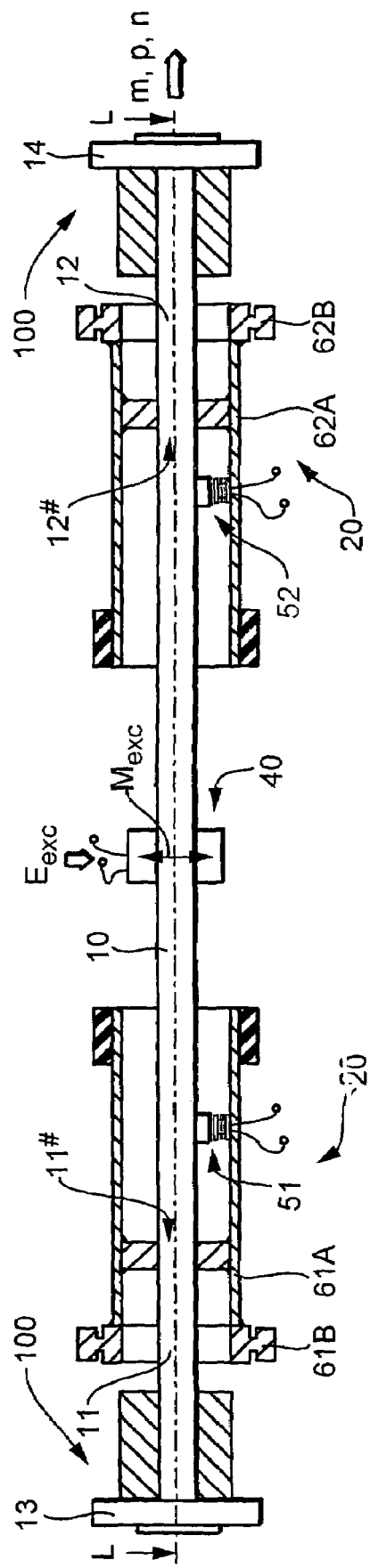
FIG. 6 is a sectional side view of another embodiment of a vibratory transducer suitable for use in the meter of FIG. 1.

As shown in FIG. 3 or 6, in yet another embodiment of the invention, torsional vibration absorber 60 comprises a first rotator 61A of predeterminable moment of inertia, coupled to flow tube 10 via a first torsion-spring body 61B of predeterminable torsional rigidity, and a second rotator 62A of predeterminable moment of inertia, coupled to flow tube 10 via a second torsion-spring body 62B of predeterminable torsional rigidity. Torsion-spring bodies 61A, 61B may be formed from thick-walled, short metal rings of suitable mass, for example, while for torsion-spring bodies 61B, 62B, short, comparatively thin-walled metal tube lengths may be used whose length, wall thickness, and cross section are so chosen that the required torsional rigidity is achieved.

For the case shown here, where the two rotators 61A, 62A, which are disposed symmetrically with respect to the midpoint of the flow tube 10, are not rigidly connected with one another, torsional vibration absorber 60 is formed by an inlet-side first absorber subunit 61 and an outlet-side second absorber subunit 62. If necessary, the two rotators may additionally be coupled directly, namely rigidly or flexibly. Consequently, rotators 61A, 62A may also be formed by a single tube enclosing the flow tube 10 and fixed to the latter by means of the two torsion springs 61B, 62B in the manner described above. For the manufacture of the two absorber subunits 61, 62, virtually the same materials as those suitable for flow tube 10 may be used, i.e., special steel, for example.

In still another embodiment of the invention, the two absorber subunits 61, 62, as shown schematically in FIGS. 7a and 7b, are formed in the manner of a cantilever and are so disposed in the transducer that a centroid $M_{61}$ of the inlet-side absorber subunit and a centroid $M_{62}$ of the outlet-side absorber subunit are spaced from flow tube 10, particularly in line with the flow tube. In this manner, mass moments of inertia applied at the respective fixing points, namely at an inlet end 11# and an outlet end 12#, eccentrically, i.e., not at the associated centroids $M_{61}$ and $M_{62}$, can be developed by means of the two absorber subunits 61, 62. This has particularly the advantage that for the case where flow tube 10, as mentioned above, is vibrated in a flexural mode, laterally acting inertial forces can be at least partially balanced, cf. in particular applicant's international Patent Application PCT/EP02/02157, which was not published prior to the filing data of the present application.

According to a further development of the invention, in order to further minimize disturbing effects on flow tube 10, torsional vibration absorber 60 comprises an antivibrator 20 extending essentially parallel to flow tube 10. Conversely, the loss of torsional vibration energy to the connected pipe is further reduced by means of antivibrator 20.

Figure 2:
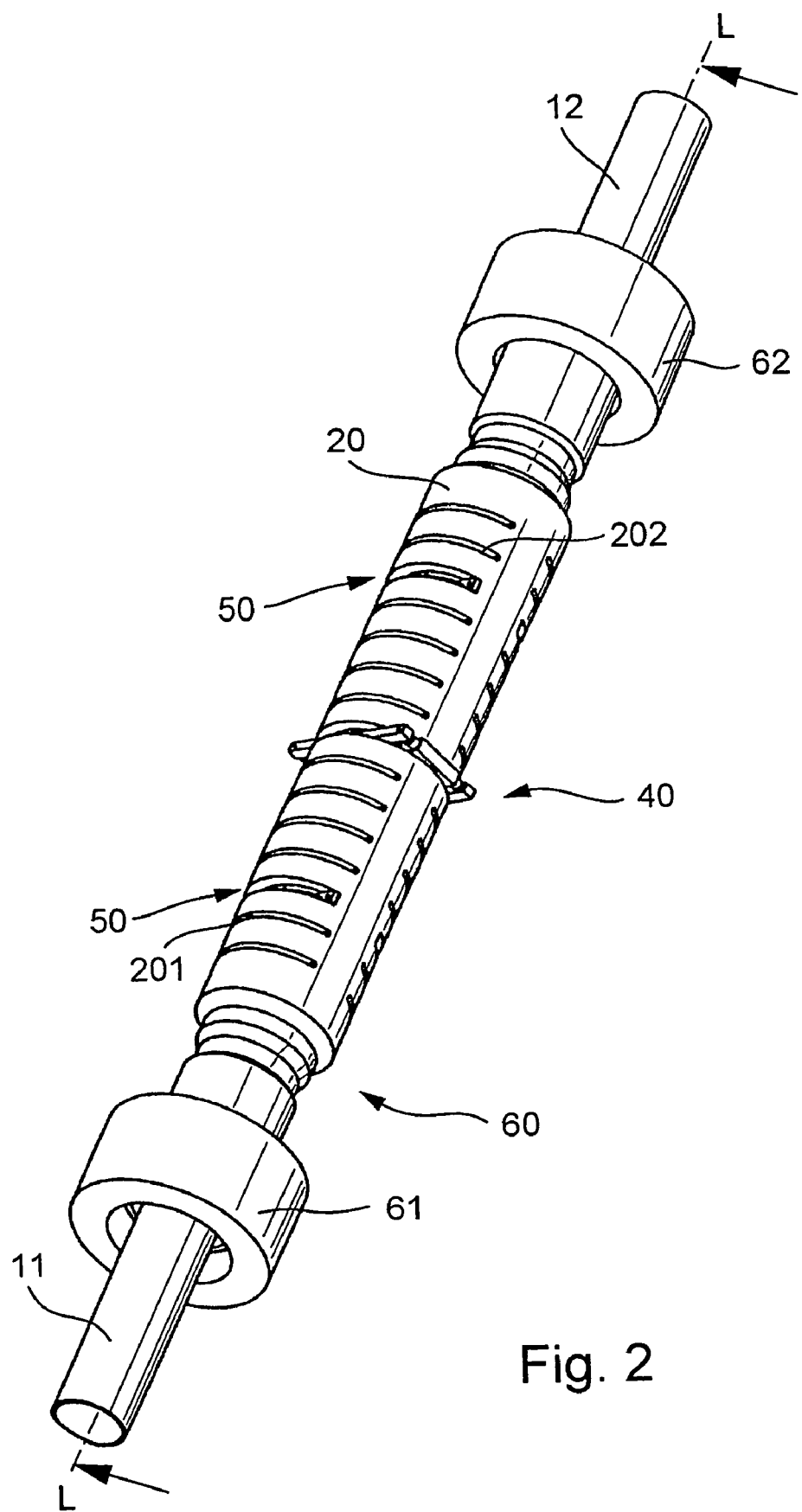
FIG. 2 is a perspective view of one embodiment of a vibratory transducer suitable for use in the meter of FIG. 1.

Antivibrator 20 may be in the form of a tube, as shown schematically in FIGS. 2 and 3, and be so connected to flow tube 10 at the inlet end 11# and outlet end 12# as to be essentially coaxial with flow tube 10, as shown in FIG. 3. Materials suitable for antivibrator 20 are virtually the same as those that can be used for flow tube 10, i.e., special steel, titanium, etc.

In this development of the invention, excitation assembly 40, as shown in FIG. 2, is advantageously so designed and so positioned in the transducer as to act on flow tube 10 and antivibrator 20 simultaneously, particularly differentially. To this end, in the embodiment shown in FIG. 4, excitation assembly 40 has at least a first excitation coil 41a, which in operation is at least intermittently traversed by the excitation current or a partial excitation current, and which is fixed to a lever 41c connected with flow tube 10 and acts differentially on flow tube 10 and antivibrator 20 via this lever 41c and an armature 41b fixed to the outside of antivibrator 20. One advantage of this arrangement is that the cross section of antivibrator 20, and hence the cross section of transducer case 100, is kept small while excitation coil 41a is easily accessible, particularly during assembly. Another advantage of this design of excitation assembly 40 is thant any cup cores 41d used, which are not negligibly heavy particularly with nominal diameter above 80 mm, can also be fixed to antivibrator 20 and thus have virtually no effect on the resonance frequencies of flow tube 10. At this point it should be noted, however, that, if necessary, it is also possible to fix excitation coil 41a to antivibrator 20, and armature 41b to flow tube 10.

Correspondingly, sensor arrangement 50 may be so designed and so positioned in the transducer that the vibrations of flow tube 10 and antivibrator 20 are sensed differentially. In the embodiment shown in FIG. 5, sensor arrangement 50 comprises a sensor coil 51a which is fixed to flow tube 10 outside all principal axes of inertia of sensor arrangement 50. Sensor coil 51a is positioned as closely as possible to an armature 51b fixed to antivibrator 20 and is so magnetically coupled to the latter that a variable measurement voltage influenced by rotational and/or lateral relative motions between flow tube 10 and antivibrator 20 is induced in the sensor coil. With the sensor coil 51a positioned in this way, both the above-mentioned torsional vibrations and the optionally excited flexural vibrations can be sensed simultaneously in an advantageous manner. If necessary, however, it is also possible to fix sensor coil 51a to antivibrator 20, and armature 51b, which is coupled to sensor coil 51a, to flow tube 10.

For the above-described case where in operation, flow tube 10 is additionally excited into flexural vibrations, antivibrator 20 may further serve to dynamically balance the transducer for a specified fluid density value, for example a value most frequently expected during operation of the transducer or a critical value, to the point that any transverse forces produced in the vibrating flow tube 10 are at least intermittently completely balanced, so that flow tube 10 will practically not leave its static rest position, cf. FIGS. 7a and 7b. Accordingly, in operation, antivibrator 20, as shown schematically in FIG. 7b, is also excited into flexural vibrations, which are essentially coplanar with the flexural vibrations of flow tube 10.

In another embodiment of the invention, a lowest torsional resonance frequency of torsional vibration absorber 60 is not greater than 1.2 times the torsional resonance frequency of flow tube 10. In a further embodiment of the invention, a lowest torsional resonance frequency of the torsional vibration absorber is not less than 0.8 times the torsional resonance frequency of flow tube 10.

In yet another embodiment of the invention, antivibrator 20 has a lowest torsional resonance frequency $f_{20}$ which is different from the respective torsional resonance frequencies $f_{61}$, $f_{62}$ of absorber subunits 61, 62. The torsional resonance frequency $f_{20}$ of antivibrator 20 may chosen to be essentially equal to the torsional frequency $f_{excT}$ at which the flow tube 10 is excited in operation. This results in flow tube 10 and antivibrator 20 vibrating torsionally out of phase with each other, namely essentially in phase opposition. At least for this case, antivibrator 20 advantageously has a torsional rigidity or torsional elasticity similar or equal to that of flow tube 10. However, it has also proved to be advantageous if the respective torsional resonance frequencies $f_{61}$, $f_{62}$ of the two absorber subunits 61, 62 are chosen to be essentially equal to the torsional frequency $f_{excT}$. For that case, the torsional resonance frequency $f_{20}$ of antivibrator 20 will advantageously be chosen to lie below or above the expected torsional vibration $f_{excT}$.

If necessary, antivibrator 20 may also be of multipart construction, as shown, for example, in U.S. Pat. No. 5,969,265, EP-A 317 340, or WO-A 00/14485, or be implemented with two separate antivibrators fixed to flow tube 10 at the inlet and outlet ends, see FIG. 6. Particularly for this case, in which antivibrator 20, serving as an internal support system, is formed by an inlet-side and an outlet-side antivibrator subunit, the external support system 100, too, may be of two-part construction, consisting of an inlet-side and an outlet-side subsystem, cf. FIG. 6.

According to a further development of the invention, as shown schematically in FIG. 3, counterbalance bodies 101, 102 are provided which, fixed to flow tube 10, permit precise setting of its torsional resonance frequencies and, thus, improved matching to the signal processing circuitry. The counterbalance bodies 101, 102 may be, for instance, metal rings slipped over flow tube 10 or metal plates fixed to the flow tube.

According to yet another development of the invention, as shown schematically in FIG. 3, grooves 201, 202 are provided in antivibrator 20 which make it possible in a simple manner to precisely set the antivibrator's torsional resonance frequencies, particularly to lower the torsional resonance frequencies by lowering the torsional rigidity of the antivibrator. While the grooves 201, 202 in FIG. 2 or 3 are shown essentially evenly distributed in the direction of the longitudinal axis L, they may also be unevenly distributed in the direction of this axis if necessary.

As is readily apparent from the above explanations, the transducer according to the invention is characterized by a multitude of possible settings which enable those skilled in the art, particularly even after specification of external and internal mounting dimensions, to achieve high-quality balancing of torsional forces produced in flow tube 10 and in antivibrator 20, and hence to minimize the loss of torsional vibration energy to the environment of the transducer.

While the invention has been illustrated and described in detail in the drawings and forgoing description, such illustration and description is to be considered as exemplary not restrictive in character, it being understood that only exemplary embodiments have been shown and described and that all changes and modifications that come within the spirit and scope of the invention as described herein are desired to protected.

What is claimed is:

1. A vibratory transducer for a fluid flowing in a pipe, comprising:
    an essentially straight flow tube communicating with the pipe for conducting the fluid, said flow tube being operable to vibrate;
    an antivibrator fixed to said flow tube, said antivibrator extending essentially parallel to said flow tube;
    an excitation assembly acting on said flow tube for vibrating said flow tube; and
    a sensor arrangement for sensing vibrations of said flow tube, said sensor arrangement being adapted to sense both torsional vibration and flexural vibrations of said flow tube wherein:
    said sensor arrangement includes a sensor coil fixed to said antivibrator and an armature fixed to said flow tube; and
    said sensor coil is magnetically coupled to said armature such that a variable measurement voltage influenced by rotational and lateral relative motions between said flow tube and said antivibrator is induced in said sensor coil.

2. The vibratory transducer as claimed in claim 1, further comprising:
    a transducer case coupled to said flow tube.

3. The vibratory transducer as claimed in claim 2, further comprising:
    a transducer case coupled to said flow tube wherein:
    said transducer case is fixed to inlet and outlet tube sections.

4. The vibratory transducer as claimed in claim 1, wherein:
    said flow tube communicates with the pipe via an inlet tube section, ending in an inlet end of said flow tube, and via an outlet tube section, ending in an outlet end of said flow tube.

5. The vibratory transducer as claimed in claim 1, wherein:
    said sensor is adapted to sense both, torsional vibrations and flexural vibrations simultaneously.

6. The vibratory transducer as claimed in claim 1, wherein:
    in operation said flow tube performs, at least intermittently, torsional vibrations about an imaginary longitudinal flow-tube axis.

7. The vibratory transducer as claimed in claim 6, wherein:
    in operation antivibrator vibrates, at least partially, out of phase with said torsionally vibrating vibration flow tube.

8. The vibratory transducer as claimed in claim 6, wherein:
    in operation said flow tube performs, at least intermittently, flexural vibrations about an imaginary longitudinal flow-tube axis.

9. The vibratory transducer as claimed in claim 6, wherein:
    in operation said flow tube performs flexural vibrations about an imaginary longitudinal flow-tube axis simultaneously with said torsional vibrations.

10. The vibratory transducer as claimed in claim 9, wherein:
    said sensor coil is adapted to sense both, torsional vibrations and flexural vibrations simultaneously.

11. The vibratory transducer as claimed in claim 10, wherein:
    the sensor coil is fixed to said antivibrator outside all principal axes of inertia of said sensor arrangement.

12. The vibratory transducer as claimed in claim 1, wherein:
    in operation said flow tube performs, at least intermittently, flexural vibrations about an imaginary longitudinal flow-tube axis.

13. The vibratory transducer as claimed in claim 1, wherein:
    said antivibrator is essentially straight.

14. The vibratory transducer as claimed in claim 13, wherein;
    said antivibrator is connected to said flow tube as to be essentially coaxial with said flow tube.

15. The vibratory transducer as claimed in claim 14, wherein:
    said antivibrator is in the form of a tube.

16. The vibratory transducer as claimed in claim 1, wherein:
    said antivibrator is in the form of a tube.

17. The vibratory transducer as claimed in claim 1, wherein:
    the sensor coil is fixed to said antivibrator outside all principal axes of inertia of said sensor arrangement.

18. A meter for measuring a viscosity of a fluid flowing in a pipe, said meter including a vibratory transducer, comprising:
    an essentially straight flow tube communicating with the pipe for conducting the fluid, said flow tube being operable to vibrate;
    an antivibrator fixed to said flow tube, said antivibrator extending essentially parallel to said flow tube;
    an excitation assembly acting on said flow tube for vibrating said flow tube; and
    a sensor arrangement for sensing vibrations of said flow tube, said sensor arrangement being adapted to sense both torsional vibrations and flexural vibrations of said flow tube wherein:
    said sensor arrangement includes a sensor coil fixed to said antivibrator and an armature fixed to said flow tube; and
    said sensor coil is magnetically coupled to said armature such that a variable measurement voltage influenced by rotational and lateral relative motions between said flow tube and said antivibrator is induced in said sensor coil.

19. A vibratory transducer for a fluid flowing in a pipe, comprising:

an essentially straight flow tube communicating with the pipe for conducting the fluid, said flow tube being operable to vibrate;

an antivibrator fixed to said flow tube, said antivibrator extending essentially parallel to said flow tube:

an excitation assembly acting on said flow tube for vibrating said flow tube; and a sensor arrangement for sensing vibrations of the flow tube said sensor arrangement being adapted to sense both torsional and flexural vibrations of said flow tube, wherein:

said sensor arrangement includes a sensor coil fixed to said flow tube and an armature fixed to said antivibrator; and said sensor coil is magnetically coupled to said armature such that a variable measurement voltage influenced by rotational and lateral relative motions between said flow tube and said antivibrator is induced in said sensor coil.

20. The vibratory transducer as claimed in claim 19, wherein:

said sensor coil is fixed to said antivibrator outside all principal axes of inertia of said sensor arrangement.

21. The vibratory transducer as claimed in claim 19, wherein:

in operation said flow tube performs, at least intermittently, torsional vibrations about an imaginary longitudinal flow-tube axis.

22. The vibratory transducer as claimed in claim 21, wherein:

in operation said flow tube performs, at least intermittently, flexural vibrations about an imaginary longitudinal flow-tube axis.

23. The vibratory transducer as claimed in claim 22, wherein:

in operation said flow tube performs flexural vibrations about an imaginary longitudinal flow-tube axis simultaneously with said torsional vibrations.

24. The vibratory transducer as claimed in claim 23, wherein:

said sensor coil is adapted to sense both, torsional vibrations and flexural vibrations simultaneously.

25. The vibratory transducer as claimed in claim 24, wherein:

the sensor coil is fixed to said antivibrator outside all principal axes of inertia of said sensor arrangement.

26. The vibratory transducer as claimed in claim 19, wherein:

in operation said flow tube performs, at least intermittently, flexural vibrations about an imaginary longitudinal flow-tube axis.

27. The vibratory transducer as claimed in claim 19, wherein:

said antivibrator is essentially straight.

28. The vibratory transducer as claimed in claim 27, wherein:

said antivibrator is connected to said flow tube as to be essentially coaxial with said flow tube.

29. The vibratory transducer as claimed in claim 28, wherein:

said antivibrator is in the form of a tube.

30. The vibratory transducer as claimed in claim 19, wherein:

said antivibrator is in the form of a tube.

31. The vibratory transducer as claimed in claim 19, wherein:

said sensor coil is adapted to sense both torsional vibrations and flexural vibrations simultaneously.

32. The vibratory transducer as claimed in claim 19, further comprising:

a transducer case coupled to said flow tube.

33. The vibratory transducer as claimed in claim 19, wherein:

said flow tube communicates with the pipe via an inlet tube section, ending in an inlet end of said flow tube, and via an outlet tube section, ending in an outlet end of said flow tube.

34. The vibratory transducer as claimed in claim 33, further comprising:

a transducer case coupled to said flow tube, wherein:

said transducer case is fixed to inlet and outlet tube sections.

35. A meter for measuring a viscosity of a fluid flowing in a pipe, said meter including a vibratory transducer comprising:

an essentially straight flow tube communicating with the pipe for conducting the fluid, said flow tube being operable to vibrate;

an antivibrator fixed to said flow tube, said antivibrator extending essentially parallel to said flow tube;

an excitation assembly acting on said flow tube for vibrating said flow tube; and a sensor arrangement for sensing vibrations of the flow tube said sensor arrangement being adapted to sense both torsional and flexural vibrations of said flow tube, wherein:

said sensor arrangement includes a sensor coil fixed to said flow tube and an armature fixed to said antivibrator; and said sensor coil is magnetically coupled to said armature such that a variable measurement voltage influenced by rotational and lateral relative motions between said flow tube and said antivibrator is induced in said sensor coil.

* * * * *